United States Patent
Piehl

(10) Patent No.: US 8,007,499 B2
(45) Date of Patent: Aug. 30, 2011

(54) VARIABLE GEOMETRY OCCIPITAL FIXATION PLATE

(75) Inventor: Jason Piehl, Apple Valley, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 0 days.

(21) Appl. No.: 12/609,868

(22) Filed: Oct. 30, 2009

(65) Prior Publication Data
US 2010/0114177 A1    May 6, 2010

Related U.S. Application Data

(63) Continuation of application No. 11/085,672, filed on Mar. 21, 2005, now Pat. No. 7,621,942.

(51) Int. Cl.
*A61B 17/80* (2006.01)
(52) U.S. Cl. .......................................... 606/71; 606/280
(58) Field of Classification Search .......... 606/280–285, 606/286–299, 70, 71
See application file for complete search history.

(56) References Cited

U.S. PATENT DOCUMENTS

| | | |
|---|---|---|
| 4,763,644 A | 8/1988 | Webb |
| 4,805,602 A | 2/1989 | Puno |
| 4,836,193 A | 6/1989 | Ransford |
| 4,841,959 A | 6/1989 | Ransford |
| 4,887,596 A | 12/1989 | Sherman |
| 4,950,269 A | 8/1990 | Gaines, Jr. |
| 5,129,388 A | 7/1992 | Vignaud |
| 5,360,429 A | 11/1994 | Jeanson et al. |
| 5,498,264 A | 3/1996 | Schlapfer et al. |
| 5,507,745 A | 4/1996 | Logroscino et al. |
| 5,520,689 A | 5/1996 | Schlapfer et al. |
| 5,531,745 A | 7/1996 | Ray |
| 5,542,946 A | 8/1996 | Logroscino et al. |
| 5,545,164 A | 8/1996 | Howland |
| 5,558,674 A | 9/1996 | Heggeness et al. |
| 5,653,708 A | 8/1997 | Howland |
| 5,665,089 A * | 9/1997 | Dall et al. ............. 606/71 |
| 5,707,372 A | 1/1998 | Errico et al. |
| 5,713,898 A | 2/1998 | Stucker et al. |
| 5,928,233 A | 7/1999 | Apfelbaum et al. |
| 5,976,135 A | 11/1999 | Sherman et al. |
| 6,017,343 A | 1/2000 | Rogozinski |

(Continued)

FOREIGN PATENT DOCUMENTS
EP    0737449 A1    10/1996

(Continued)

OTHER PUBLICATIONS

Examination Report for European Patent Application No. 06738970.0, dated Oct. 21, 2010, European Patent Office, 7 pgs.

(Continued)

*Primary Examiner* — Eduardo C Robert
*Assistant Examiner* — Jan Christopher Merene
(74) *Attorney, Agent, or Firm* — Sprinkle IP Law Group

(57) ABSTRACT

A fixation device for connecting a stabilization device to a bone comprises a first member comprising a first portion for attachment to a bone; a second member comprising a second portion for attachment to a bone and connected to the first member by a pivotal connection such that the first and second portions are spaced apart by an adjustable distance, at least one of the first and second members further comprising a portion for mounting a connector adapted to secure a stabilization device.

11 Claims, 6 Drawing Sheets

U.S. PATENT DOCUMENTS

| | | | |
|---|---|---|---|
| 6,077,262 | A | 6/2000 | Schlapfer et al. |
| 6,096,040 | A * | 8/2000 | Esser .......................... 606/280 |
| 6,146,382 | A | 11/2000 | Hurlbert |
| 6,187,005 | B1 | 2/2001 | Brace et al. |
| 6,206,882 | B1 * | 3/2001 | Cohen .......................... 606/283 |
| 6,238,396 | B1 | 5/2001 | Lombardo |
| 6,296,644 | B1 | 10/2001 | Saurat et al. |
| 6,302,883 | B1 | 10/2001 | Bono |
| 6,315,779 | B1 | 11/2001 | Morrison |
| 6,336,927 | B2 | 1/2002 | Rogozinski |
| 6,368,351 | B1 | 4/2002 | Glenn et al. |
| 6,379,358 | B1 | 4/2002 | Kuo |
| 6,432,109 | B1 | 8/2002 | Letendart et al. |
| 6,485,491 | B1 | 11/2002 | Farris et al. |
| 6,524,315 | B1 | 2/2003 | Selvitelli et al. |
| 6,547,790 | B2 | 4/2003 | Harkey, III et al. |
| 6,620,164 | B2 | 9/2003 | Ueyama et al. |
| 6,682,532 | B2 | 1/2004 | Johnson |
| 6,832,999 | B2 | 12/2004 | Ueyama et al. |
| 6,902,565 | B2 | 6/2005 | Berger et al. |
| 6,949,123 | B2 | 9/2005 | Reiley |
| 6,958,065 | B2 | 10/2005 | Ueyama et al. |
| 7,033,377 | B2 | 4/2006 | Miller |
| 7,060,069 | B2 | 6/2006 | Kozak et al. |
| 7,232,441 | B2 | 6/2007 | Altarac et al. |
| 7,250,052 | B2 | 7/2007 | Landry et al. |
| 7,303,563 | B2 | 12/2007 | Poyner et al. |
| 7,491,218 | B2 | 2/2009 | Landry et al. |
| 7,618,443 | B2 | 11/2009 | Abdou |
| 7,621,942 | B2 | 11/2009 | Piehl |
| 7,857,836 | B2 | 12/2010 | Huebner |
| 7,901,433 | B2 | 3/2011 | Forton et al. |
| 2002/0049446 | A1 | 4/2002 | Harkey, III |
| 2002/0120268 | A1 | 8/2002 | Berger |
| 2003/0004512 | A1 | 1/2003 | Farris et al. |
| 2003/0036759 | A1 | 2/2003 | Musso |
| 2003/0153913 | A1 | 8/2003 | Altarac et al. |
| 2003/0163132 | A1 | 8/2003 | Chin |
| 2003/0176863 | A1 | 9/2003 | Ueyama et al. |
| 2004/0122426 | A1 | 6/2004 | Michelson |
| 2004/0127904 | A1 | 7/2004 | Konieczynski et al. |
| 2004/0153070 | A1 | 8/2004 | Barker et al. |
| 2004/0172022 | A1 | 9/2004 | Landry |
| 2004/0267259 | A1 | 12/2004 | Mazda et al. |
| 2005/0010227 | A1 | 1/2005 | Paul |
| 2005/0080417 | A1 | 4/2005 | Alexis et al. |
| 2005/0119656 | A1 | 6/2005 | Ferrante et al. |
| 2005/0124994 | A1 | 6/2005 | Berger et al. |
| 2005/0216005 | A1 | 9/2005 | Howland |
| 2005/0216008 | A1 * | 9/2005 | Zwirnmann et al. ............ 606/69 |
| 2005/0228382 | A1 | 10/2005 | Richelsoph et al. |
| 2005/0240185 | A1 | 10/2005 | Boomer et al. |
| 2005/0251141 | A1 | 11/2005 | Frigg et al. |
| 2005/0273104 | A1 | 12/2005 | Oepen et al. |
| 2005/0277939 | A1 | 12/2005 | Miller |
| 2005/0283153 | A1 | 12/2005 | Poyner et al. |
| 2005/0288669 | A1 | 12/2005 | Abdou |
| 2006/0004359 | A1 | 1/2006 | Kramer et al. |
| 2006/0004360 | A1 | 1/2006 | Kramer et al. |
| 2006/0004363 | A1 | 1/2006 | Brockmeyer et al. |
| 2006/0155283 | A1 | 7/2006 | Doherty et al. |
| 2006/0155284 | A1 | 7/2006 | Doherty et al. |
| 2006/0184170 | A1 | 8/2006 | Kapitan et al. |
| 2006/0217710 | A1 | 9/2006 | Abdou |
| 2006/0217723 | A1 | 9/2006 | Suh |
| 2006/0217724 | A1 | 9/2006 | Suh |
| 2006/0229610 | A1 | 10/2006 | Piehl |
| 2006/0264932 | A1 | 11/2006 | Bert |
| 2007/0016189 | A1 | 1/2007 | Lake |
| 2007/0083201 | A1 | 4/2007 | Jones et al. |
| 2007/0118121 | A1 | 5/2007 | Purcell et al. |
| 2007/0123872 | A1 | 5/2007 | Brockmeyer et al. |
| 2007/0299441 | A1 | 12/2007 | Hoffman |
| 2008/0051783 | A1 | 2/2008 | Null et al. |
| 2008/0086124 | A1 | 4/2008 | Forton |
| 2008/0147123 | A1 | 6/2008 | Schermerhorn |
| 2008/0177314 | A1 | 7/2008 | Lemoine |
| 2008/0300635 | A1 | 12/2008 | Lieponis |
| 2009/0270924 | A1 | 10/2009 | Wing et al. |

FOREIGN PATENT DOCUMENTS

| | | |
|---|---|---|
| EP | 1180348 A2 | 2/2002 |
| FR | 2687561 A1 | 2/1992 |
| FR | 2760629 A1 | 3/1997 |
| WO | WO 95/31147 A1 | 11/1995 |
| WO | WO 97/23170 A1 | 7/1997 |
| WO | WO 98/41160 A1 | 9/1998 |
| WO | WO 2005/122922 A2 | 12/2005 |
| WO | WO 2006/019370 A1 | 2/2006 |
| WO | WO 2006/096756 A2 | 9/2006 |
| WO | WO 2006/102222 A2 | 9/2006 |
| WO | WO 2006/102222 A3 | 9/2006 |
| WO | WO 2007/044716 A1 | 4/2007 |
| WO | WO 2007/146482 A2 | 12/2007 |
| WO | WO 2008/042633 A2 | 4/2008 |

OTHER PUBLICATIONS

Office Action issued in U.S. Appl. No. 11/616,720 mailed Nov. 9, 2010, 11 pgs.
Office Action issued in U.S. Appl. No. 11/616,720 mailed Dec. 24, 2009, 11 pgs.
Office Action issued in U.S. Appl. No. 11/756,106 mailed Feb. 19, 2010, 6 pgs.
Office Action issued in U.S. Appl. No. 11/542,786 mailed Mar. 15, 2010, 9 pgs.
Office Action issued in U.S. Appl. No. 11/616,720 mailed Jun. 10, 2010, 10 pgs.
Office Action issued in U.S. Appl. No. 11/756,106 mailed Sep. 1, 2010, 7 pgs.
Notice of Allowance issued in U.S. Appl. No. 11/542,786 mailed Aug. 26, 2010, 4 pgs.
Summit SI OCT Spinal Fixation System, undated, 2 pgs.
Stryker Spine Products, "Products: Cervical OASYS" Webpage, undated, 1 pg.
Blackstone Ascent, Production Information Page, undated, 1 pg.
Office Action issued in U.S. Appl. No. 11/085,672 mailed Nov. 17, 2006, 9 pgs.
Interpore Cross International, "Introducing the Altrius OCT System," Biological & Structural Innovation, Interpore Cross Intl, Irvine, CA, Copyright 2003, 2 pgs.
Blackstone Medical Inc., "Ascent Posterior Occipital Cervico-Thoracic System," Cervical and Thoracolumbar Systems, www.blackstonemedical.com., Copyright 2005, 1 pg.
Globus Medical, Cervical Webpage, Copyright 2005, downloaded from http://www.globusmedical.com/products/cervical.php, on Feb. 2, 2006, 1 pg.
Globus Medical, Protex CT . . . the new standard in OCT Stabilization systems, www.globusmedical.com, 1-866-456-2871, undated, 1 pg.
Depuy Spine, "Mountaineer OCT Spinal System," Copyright 2006, DePuy Spine, Inc., Raynham, MA, Mar. 2005, 6 pgs.
Office Action issued in U.S. Appl. No. 11/085,672 mailed May 18, 2007, 15 pgs.
Office Action issued in U.S. Appl. No. 11/085,672 mailed Nov. 1, 2007, 8 pgs.
International Search Report and Written Opinion issued in International Application No. PCT/US2007/066039, mailed Apr. 14, 2008, 11 pgs.
International Search Report and Written Opinion in PCT/US2007/079295 mailed Apr. 17, 2008, 14 pgs.
Office Action issued in U.S. Appl. No. 11/085,672 mailed Apr. 29, 2008, 9 pgs.
Office Action issued in U.S. Appl. No. 11/423,201 mailed Sep. 3, 2008, 15 pgs.
Office Action issued in U.S. Appl. No. 11/085,672 mailed Oct. 31, 2008, 9 pgs.
Office Action issued in U.S. Appl. No. 11/423,201 mailed Dec. 10, 2008, 17 pgs.

International Preliminary Report on Patentability issued in International Application No. PCT/US2007/066039, mailed Dec. 10, 2008, 6 pgs.
Office Action issued in U.S. Appl. No. 11/423,201 mailed Mar. 5, 2009, 15 pgs.
Office Action issued in U.S. Appl. No. 11/542,786 mailed Mar. 5, 2009, 7 pgs.
Office Action issued in U.S. Appl. No. 11/085,672 mailed May 7, 2009, 12 pgs.
Office Action issued in U.S. Appl. No. 11/563,902 mailed May 8, 2009, 9 pgs.
International Search Report and Written Opinion, International Application No. PCT/US2006/009996 mailed Jul. 19, 2007, 10 pgs.
International Preliminary Report on Patentability, International Application No. PCT/US2006/009996, mailed Sep. 25, 2007, 8 pgs.
International Preliminary Report on Patentability, International Application No. PCT/US2007/079295, mailed Apr. 7, 2009, 7 pgs.
Office Action issued in U.S. Appl. No. 11/616,720 mailed May 27, 2009, 8 pgs.
International Preliminary Report on Patentability, Chapter I, mailed Jun. 30, 2009, International Application No. PCT/US2007/085190, 8 pgs.
International Search Report and Written Opinion mailed Jun. 3, 2008, International Application No. PCT/US2007/085190, 13 pgs.
Office Action issued in U.S. Appl. No. 11/756,106 mailed Aug. 26, 2009, 8 pgs.
Office Action issued in U.S. Appl. No. 11/542,786 mailed Sep. 30, 2009, 8 pgs.
Office Action issued in U.S. Appl. No. 11/563,902 mailed Oct. 27, 2009, 10 pgs.
Office Action issued in U.S. Appl. No. 11/423,201 mailed Oct. 29, 2009, 11 pgs.
Office Action for U.S. Appl. No. 11/563,902 mailed Jan. 31, 2011, 12 pgs.
Office Action for U.S. Appl. No. 11/756,106 mailed Feb. 15, 2011, 8 pgs.
Office Action for U.S. Appl. No. 11/563,902, mailed Jun. 7, 2011, 19 pgs.

* cited by examiner

VARIABLE GEOMETRY OCCIPITAL FIXATION PLATE

CROSS-REFERENCE TO RELATED APPLICATION(S)

This application is a continuation of, and claims a benefit of priority under 35 U.S.C. 120 of the filing date of U.S. patent application Ser. No. 11/085,672, entitled "VARIABLE GEOMETRY OCCIPITAL FIXATION PLATE," filed Mar. 21, 2005, now U.S. Pat. No. 7,621,942, the entire contents of which are hereby expressly incorporated by reference for all purposes.

TECHNICAL FIELD

The present invention relates generally to fixation devices used in orthopedic surgery. This invention relates more particularly to devices used for cervical posterior fixation by means of a plate attached to a bone in the occipital region and secured to a rod which attaches to a cable, wire, plate, or screw fastened in the spinal region.

BACKGROUND

Fixation devices are used in orthopedic surgery to stabilize bones such as those in the spinal column. One type of fixation device includes a plate attachable to a portion of a bone. The plate may be connected to another bone or another portion of the same bone, directly or through other connecting devices. For example, posterior fixation devices can include a plate fastened to the skull, or occiput, one or more rods running longitudinally along the spine and connected to the plate, and plates, cables, wires, hooks, screws, or other connectors attached to a vertebra and connected to the rod.

A number of such mechanisms are known in the act. To accommodate the variation in patient size and anatomy, a plate often needs to be chosen from a set of plates of multiple sizes and/or varying geometry. This results in a higher cost of the device assembly and a need to maintain separate inventory of the various size and geometry devices. It also increases the surgical time because the surgeon must search for the device that best fits the patient. Accordingly, there is a need for an improved fixation plate.

SUMMARY

A fixation device for connecting a stabilization device to a bone comprises a first member comprising a first portion for attachment to a bone; a second member comprising a second portion for attachment to a bone and connected to the first member by a pivotal connection such that the first and second portions are spaced apart by an adjustable distance, at least one of the first and second members further comprising a portion for mounting a connector adapted to secure a stabilization device A method of attaching a stabilization device to a bone comprises attaching a first plate to a bone at a first portion on the first plate; attaching a second plate, pivotally attached to the first plate, to a bone at a second portion on the second plate; pivotally adjusting the position of the second plate relative to the first plate to adjust the distance between the first portion and the second portion; and attaching a stabilization device to either the first plate or the second plate.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Figure 1:
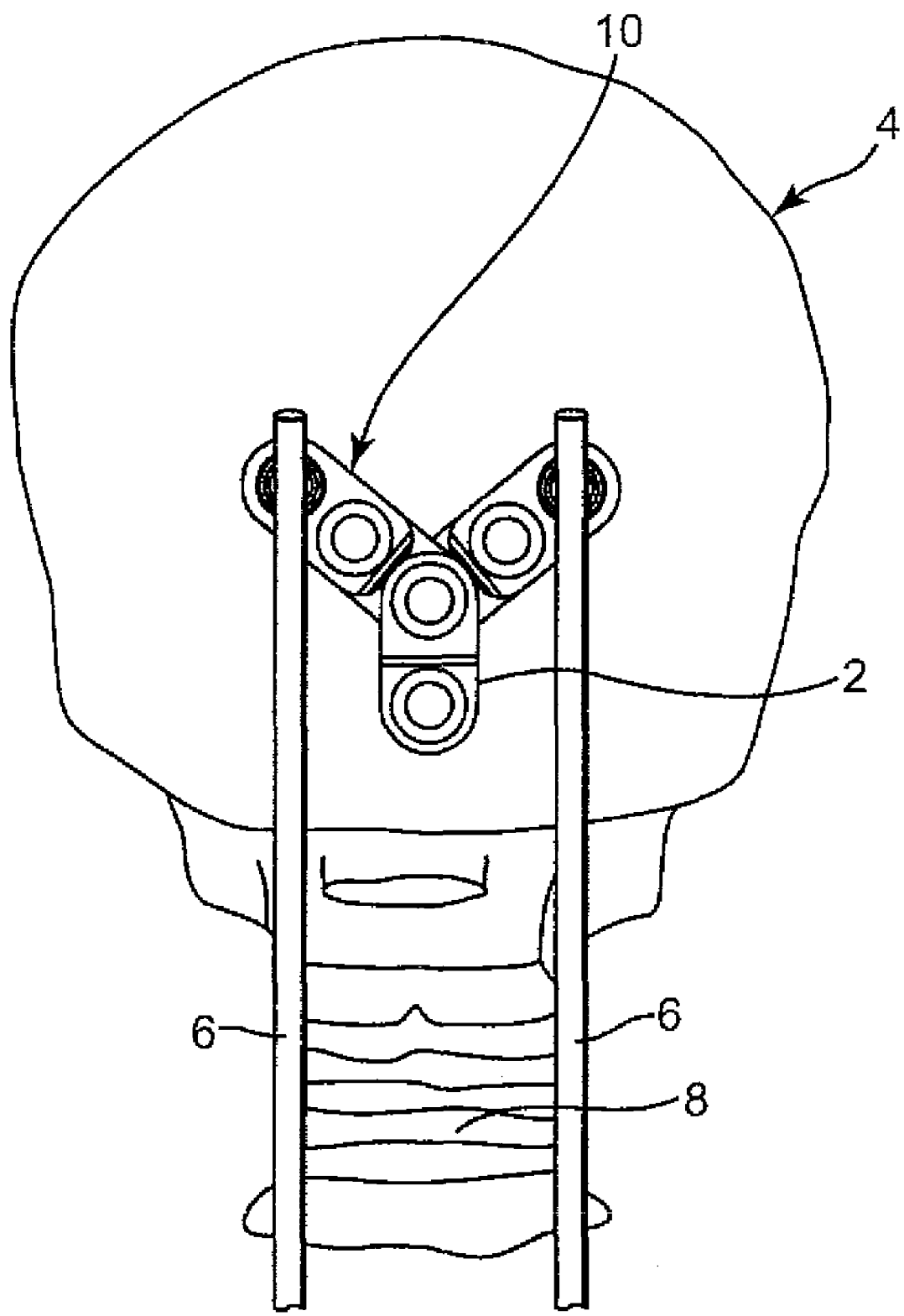
FIG. 1 shows a variable geometry occipital device, according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a variable geometry occipital device 10 in one embodiment of the present invention. The variable geometry occipital device 10 in this case is affixed to the occiput 2 of the patient 4. One or more rods 6 are attached to the device 10 and run substantially along the spine column 8 and are attached to various segments of the spinal column 8.

Figure 2:
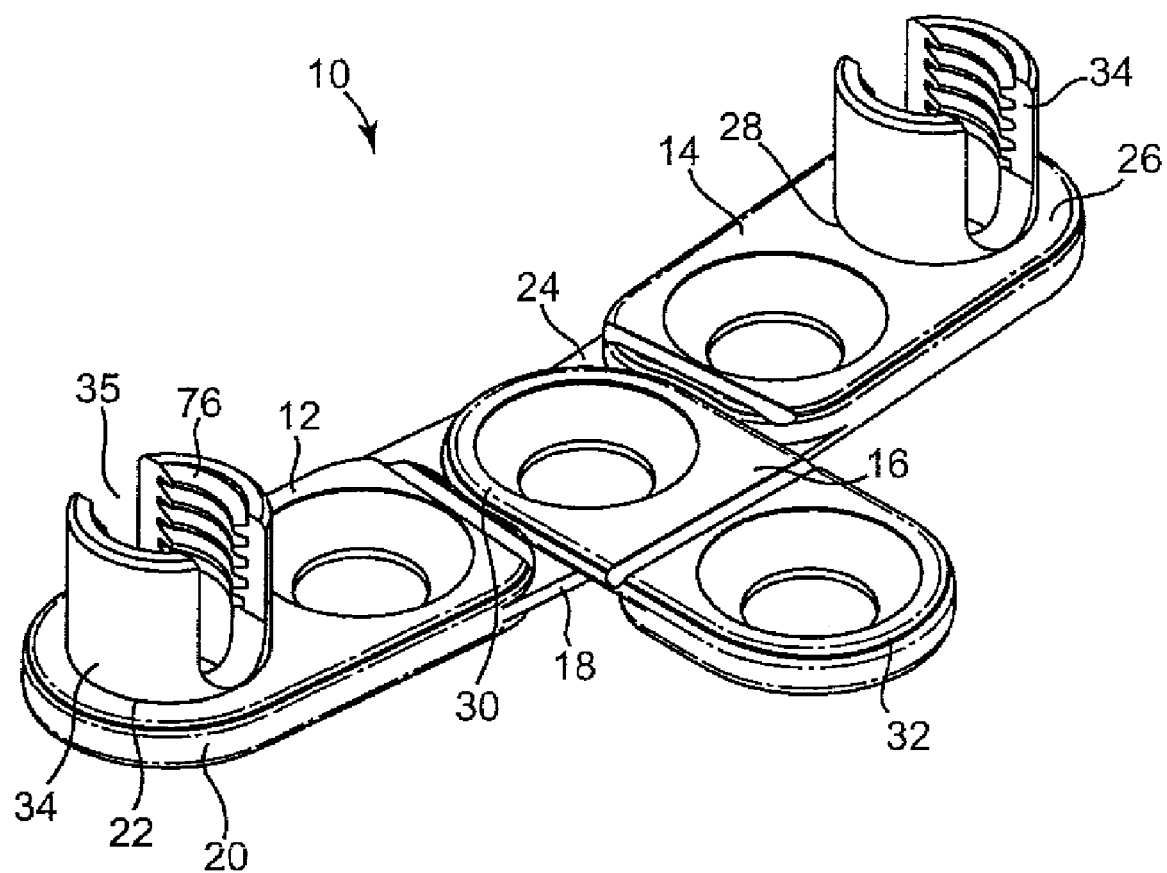
FIG. 2 shows a perspective view of the variable geometry occipital fixation device of FIG. 1

FIG. 2 shows a perspective view of the variable geometry occipital device 10 of FIG. 1. The variable geometry occipital fixation device 10 includes a first lateral member 12, a second lateral member 14, and a midline member 16. The first lateral member includes a proximal end 18, a distal end 20, and an attachment bore 22 located at the distal end 20.

The second lateral member includes a proximal end 24, a distal end 26, and an attachment bore 28 located at the distal end 26. The midline member includes a proximal end 30 and a distal end 32. In the embodiment shown in FIG. 2, the proximal ends 18, 24, and 30 are stacked on top of each other. Attachment bosses 34 are inserted into the attachment bores 22 and 28. Each attachment boss 34 has a slot 35 for receiving a stabilization device such as a rod, a cable or a cord. The attachment boss 34 further has a threaded portion 76 for receiving a threaded fastener, such as a set screw, which can be tightened directly or indirectly (e.g., through a spacer) against the stabilization device to retain it in the slot 35. Any other suitable connectors for securing stabilization devices can be used instead of the attachment bosses 34 to achieve the desired performance.

Figure 3:
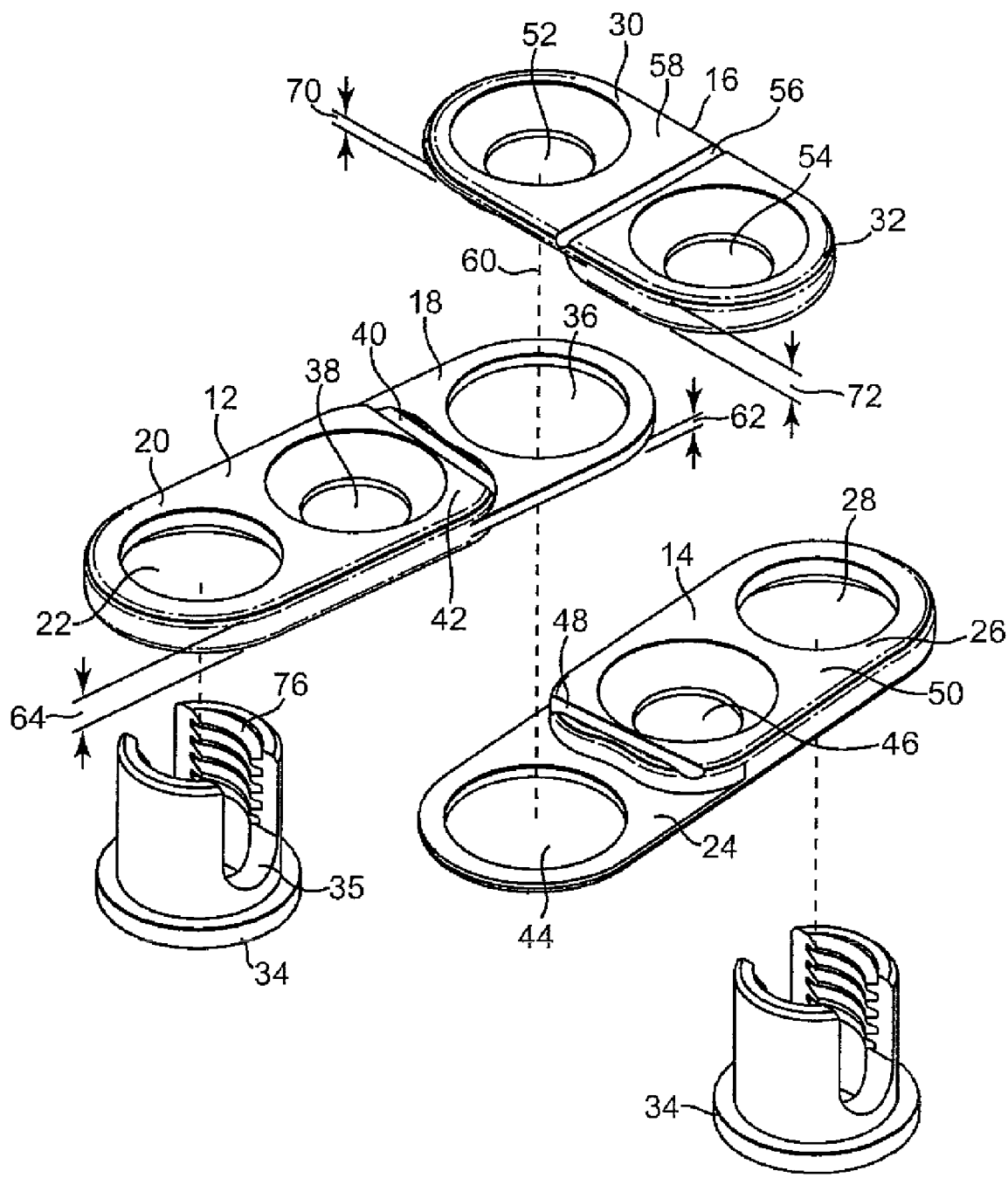
FIG. 3 shows an exploded view of the variable geometry occipital fixation device of FIG. 1.

FIG. 3 shows an exploded view of the variable geometry occipital fixation device 10 of FIG. 1. The first lateral member 12 includes the attachment bore 22, a pivot bore 36 located at the proximal end 18, and a fixation bore 38 interposed between the attachment bore 22 and the pivot bore 36. A groove 40 is interposed between the proximal end 18 and the distal end 20. The groove 40 facilitates bending of the first lateral member 12 so that it conforms to the occiput. In the embodiment shown in FIG. 3, the groove 40 is located on a top surface 42. The groove 40 could alternatively be located in any other suitable area. Alternatively, the first lateral member 12 could have more than one groove 40, or no groove at all.

Similarly, the second lateral member 14 includes a pivot bore 44 located at the proximal end 24, the attachment bore 28 located at the distal end 26, and a fixation bore 46 interposed between the attachment bore 28 and the pivot bore 44. A groove 48 is interposed between the proximal end 24 and the distal end 26 and is located on a top surface 50. Alternatively, the groove 48 could be located in some other suitable area. The second lateral member 14 could include any appropriate number of grooves 48.

The midline member 16 includes a proximal end 30 and a distal end 32. A pivot bore 52 is located at the proximal end 30 and a fixation bore 54 is located at the distal end 32. A groove 56 is interposed between the proximal end 30 and the distal end 32 and is located on a top surface 58. The midline member 16 could include any appropriate number of grooves 56 located in any suitable area.

In the embodiment shown in FIGS. 1-3, the pivot bores 36, 44, and 52 are aligned so that the first lateral member 12 and the second lateral member 14 rotate around a common axis 60. The thickness 62 of the proximal end 18 of the first lateral member 12 is less than the thickness 64 of the distal end 20. Similarly, the thickness 66 of the proximal end 24 of the second lateral member 14 is less than the thickness 68 of the distal end 26. The thickness 70 of the proximal end 30 of the midline member 16 is also less than the thickness 72 of the distal end 32. In this manner, when the three members 12, 14, and 16 are assembled together and installed in the patient 4, the thickness of the occipital device 10 is substantially uniform across the members 12, 14, and 16 and the stacked portions of members 12, 14, and 16. However, the invention is not limited to a device of such uniform thickness. The thicknesses 64, 68, and 72 need not be less than the thicknesses 66, 70, and 74 or be less by the same amounts as in this illustrative embodiment of the invention.

In the embodiment shown in FIGS. 1-3, the fixation bore 38 in the first lateral member 12 is countersunk so that when a fastener (not shown) is inserted into fixation bore 38, the height of the fastener protruding above the top surface 42 is minimized. The fixation bores 46 and 54 in the second lateral member 14 and the midline member 16 are also countersunk in a similar manner. Alternatively, some or all of the fixation bores 38, 46, and 54 need not be countersunk.

The three members 12, 14, and 16 can be attached to each other in a number of ways. In one embodiment of the invention, the members are swaged together so that they remain attached to each other while being handled but can be manipulated into different angular relationships to each other. Alternatively, the three members 12, 14, and 16 can remain separate until implantation into the patient 4, when they become linked to one another by the insertion of a fastener (not shown) into the pivot bores 36, 44, and 52. The fastener could be a rivet, screw, or any other suitable fastener.

Figure 4:
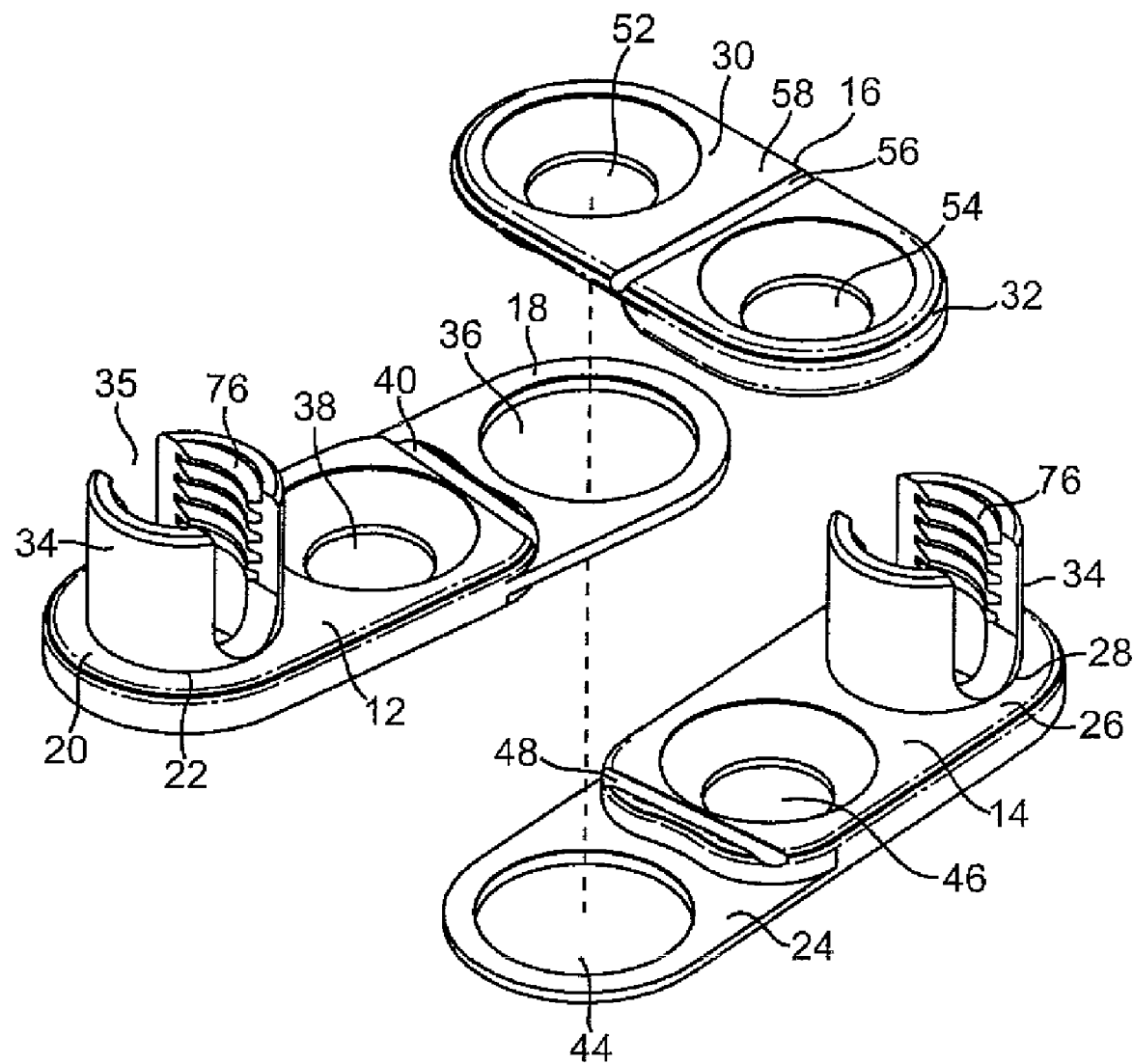
FIG. 4 shows another exploded view of the variable geometry occipital fixation device of FIG. 1 after insertion of the attachment bosses.

FIG. 4 is a perspective and partially exploded view of the variable geometry occipital fixation device 10 of FIG. 1 after insertion of the attachment bosses 34 into attachment bores 22 and 28. In the embodiment shown in FIG. 4, the attachment bosses 34 are inserted into the attachment bores 22 and 28. The attachment bosses 34 could be press-fit, riveted or swaged into the attachment bores 22 and 28 or inserted in any other suitable manner. The attachment bosses 34 preferably are free to rotate inside of the bores 22 and 28 so as to maintain the orientation of the stabilization device after the orientations of the lateral members 12 and 14 are adjusted.

Figure 5A:
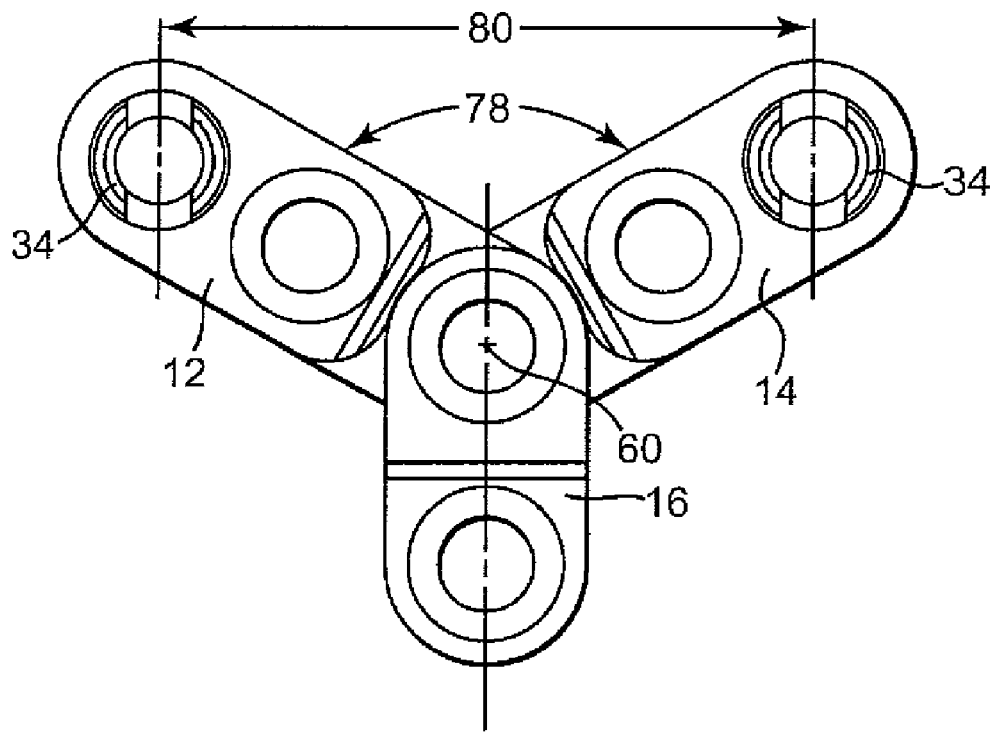
FIG. 5A shows a top plan view of the variable geometry occipital fixation device of FIG. 1 in its narrowest configuration.

FIG. 5A shows a top plan view of the variable geometry occipital fixation device 10 shown in a narrow configuration. As shown in FIG. 5A, the angle 78 between the lateral members 12 and 14 is relatively small, thereby reducing the distance 80 between the bosses 34. The angle 78 can vary as needed achieve the desired distance 80.

Figure 5B:
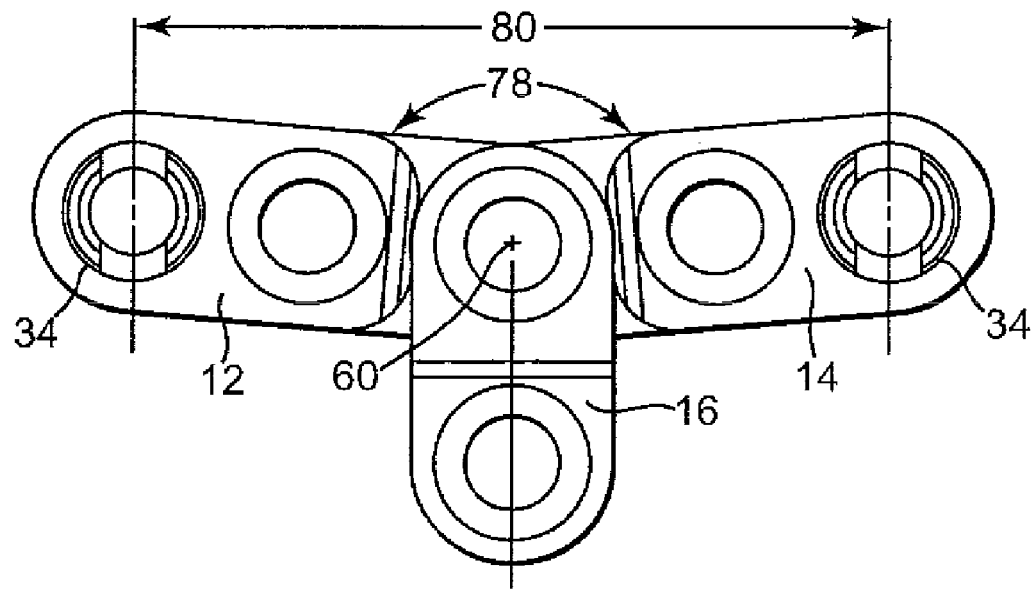
FIG. 5B shows a top plan view of the variable geometry occipital fixation device of FIG. 1 in its widest configuration.

FIG. 5B shows a top plan view of the variable geometry occipital fixation device 10 shown in a wide configuration. As shown in FIG. 5B, the angle 78 between the lateral members 12 and 14 is larger than the angle 78 shown in FIG. 5A, thereby spanning a larger distance 80 between the bosses 34 than shown in FIG. 5A. In one embodiment of the present invention, the angle 78 is approximately 100 degrees when the distance 80 is minimized and is approximately 170 degrees when the distance 80 is maximized. The available range for angle 80 need not be limited to these angles, but instead can include any desirable range.

The first and second lateral members 12 and 14 and the midline member 16 can include any configuration of fixation bores, attachment bores, and pivot bores suitable for achieving the desired variability in the distance 78 between the attachment bores 24 and 38. The number and the location of the fixation bores, attachment bores, and pivot bores can vary as needed.

Figure 6:
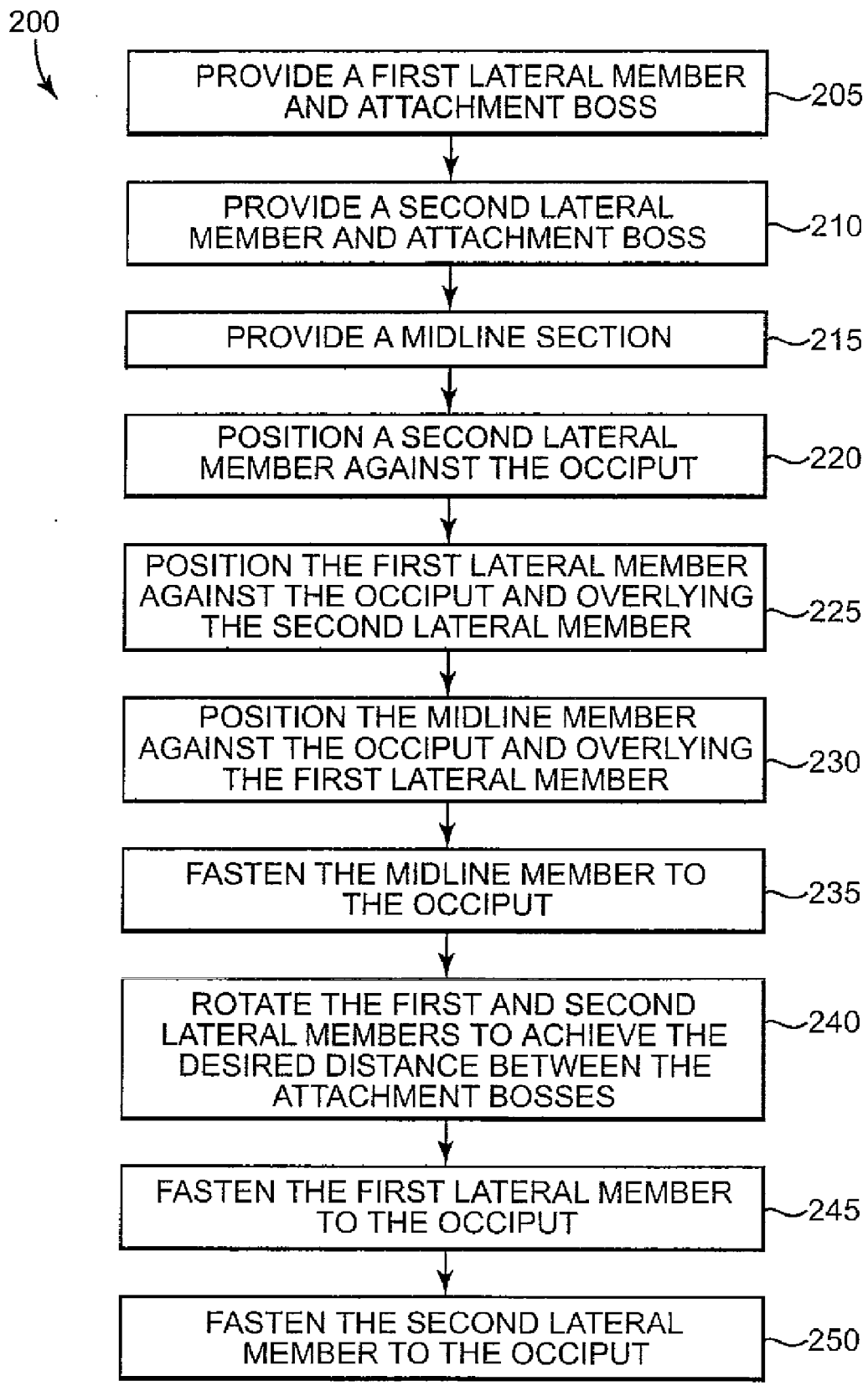
FIG. 6 shows an exemplary method of using the variable geometry occipital fixation device of FIG. 1.

FIG. 6 shows an exemplary method 200 of using the occipital fixation bracket 10 of the present invention. A first lateral member 12 and a first attachment boss 34 are provided (block 205). Then, a second lateral member 14 and a second attachment boss 34 are provided (block 210). The attachment bosses 34 are preferably inserted into the first and second lateral members 12 and 14 prior to surgery. A midline section 16 is also provided (block 215).

The second lateral member 14 is positioned in the desired location against the occiput (block 220). The first lateral member 12 is positioned against the occiput and overlying the second lateral member 14 so that the pivot bores 36 and 44 rotate around a common axis 60 (block 225). The midline member 16 is then positioned against the occiput and overlying the first lateral member 12 (block 230). The pivot bore 52 is aligned with the pivot bores 36 and 44, Next, fasteners are inserted through the pivot bore 52 and the fixation bore 54 of the midline member 16 and into the occiput, thereby attaching the midline member 16 to the occiput (block 235). The first lateral member 12 and the second lateral member 14 are rotated around the common axis 60 until the desired distance 80 between the attachment bosses 34 is achieved (block 240). The attachment bosses 34 are free to rotate in their bores 22 and 28. The fasteners are then inserted into the fixation bores 38 and 46 of the first and second lateral members 12 and 14, thereby fastening them to the occiput and fixing the position of the attachment bosses 34 (blocks 245 and 250). In this manner, the variable geometry occipital fixation device may be installed and adjusted to accommodate a variety of patient sizes and anatomy.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

What is claimed is:

1. A variable geometry occipital fixation device, comprising:
   a first lateral member having a proximal end, a distal end, a pivot bore located at the proximal end, and an attachment bore located at the distal end;
   a second lateral member having a proximal end, a distal end, a pivot bore located at the proximal end, and an attachment bore located at the distal end; and
   a single-piece midline member having a proximal end, a distal end, a pivot bore located at the proximal end, and a fixation bore located at the distal end, wherein the distal end of the first lateral member is thicker than the proximal end of the first lateral member, wherein the distal end of the second lateral member is thicker than the proximal end of the second lateral member, and wherein the distal end of the midline member is thicker than the proximal end of the midline member, wherein in forming the variable geometry occipital fixation device, the proximal ends of the first lateral member, the second lateral member, and the midline member are stacked on top of each other along a common axis extending through the pivot bores of the first lateral member, the second lateral member, and the midline member such that a thickness of the variable geometry fixation device is substantially uniform across the first lateral member, the second lateral member, and the midline member, and wherein the first lateral member, the second lateral member, the midline member, or a combination thereof is rotatable about the common axis.

2. The variable geometry occipital fixation device of claim 1, wherein the first lateral member further comprises a fixation bore interposed between the attachment bore and the pivot bore.

3. The variable geometry occipital fixation device of claim 2, wherein the second lateral member further comprises a fixation bore interposed between the attachment bore and the pivot bore.

4. The variable geometry occipital fixation device of claim 3, wherein the fixation bore of the first lateral member is countersunk into the first lateral member, wherein the fixation bore of the second lateral member is countersunk into the second lateral member, and wherein the fixation bore of the midline member is countersunk into the midline member.

5. The variable geometry occipital fixation device of claim 1, wherein the first lateral member further comprises one or more grooves interposed between the proximal end and the distal end of the first lateral member to facilitate bending of the first lateral member.

6. The variable geometry occipital fixation device of claim 5, wherein the second lateral member further comprises one or more grooves interposed between the proximal end and the distal end of the second lateral member to facilitate bending of the second lateral member.

7. The variable geometry occipital fixation device of claim 1, wherein the midline member further comprises one or more grooves interposed between the proximal end and the distal end of the midline member to facilitate bending of the midline member.

8. The variable geometry occipital fixation device of claim 1, wherein the proximal end of the first lateral member, the proximal end of the second lateral member, and the proximal end of the midline member are swaged together or linked together through a fastener inserted into the pivot bore of the first lateral member, the pivot bore of the second lateral member, and the pivot bore of the midline member.

9. The variable geometry occipital fixation device of claim 1, further comprising:
   a first attachment boss inserted into the attachment bore of the first lateral member and having a slot for receiving a first spinal stabilization device; and
   a second attachment boss inserted into the attachment bore of the second lateral member and having a slot for receiving a second spinal stabilization device.

10. The variable geometry occipital fixation device of claim 9, wherein the first attachment boss comprises a threaded portion for receiving a first threaded fastener.

11. The variable geometry occipital fixation device of claim 9, wherein the first attachment boss inserted into the attachment bore of the first lateral member is free to rotate inside of the attachment bore of the first lateral member.

* * * * *